United States Patent
Tillinghast et al.

[11] Patent Number: 5,921,946
[45] Date of Patent: Jul. 13, 1999

[54] JOINT BRACE HINGES

[75] Inventors: Theodore V. Tillinghast, Carlsbad; Charles A. Bastyr, Del Mar; Kevin D. Simmons, San Diego, all of Calif.

[73] Assignee: Smith & Nephew, Inc., Memphis, Tenn.

[21] Appl. No.: 08/955,648

[22] Filed: Oct. 22, 1997

[51] Int. Cl.⁶ ........................................ A61F 5/00
[52] U.S. Cl. ............................... 602/16; 602/26
[58] Field of Search ................. 602/5, 16, 20, 602/23, 26

[56] References Cited

U.S. PATENT DOCUMENTS

| | | |
|---|---|---|
| 3,898,709 | 8/1975 | Lewis et al. . |
| 4,088,130 | 5/1978 | Applegate . |
| 4,337,764 | 7/1982 | Lerman . |
| 4,340,041 | 7/1982 | Frank . |
| 4,372,298 | 2/1983 | Lerman . |
| 4,433,679 | 2/1984 | Mauldin et al. . |
| 4,463,751 | 8/1984 | Bledsoe . |
| 4,489,718 | 12/1984 | Martin . |
| 4,531,515 | 7/1985 | Rolfes . |
| 4,554,913 | 11/1985 | Womack et al. . |
| 4,599,998 | 7/1986 | Castillo . |
| 4,612,919 | 9/1986 | Best . |
| 4,614,181 | 9/1986 | Karlsson . |
| 4,620,532 | 11/1986 | Houswerth . |
| 4,632,096 | 12/1986 | Harris . |
| 4,697,583 | 10/1987 | Mason et al. . |
| 4,723,539 | 2/1988 | Townsend . |
| 4,732,143 | 3/1988 | Kansek et al. . |
| 4,773,404 | 9/1988 | Townsend . |
| 4,777,941 | 10/1988 | Borig et al. . |
| 4,791,916 | 12/1988 | Paez . |
| 4,817,588 | 4/1989 | Bledsoe . |
| 4,856,501 | 8/1989 | Castillo et al. . |
| 4,890,607 | 1/1990 | Townsend . |
| 4,940,044 | 7/1990 | Castillo . |
| 4,982,732 | 1/1991 | Morris . |
| 5,000,169 | 3/1991 | Swicegood et al. . |
| 5,000,170 | 3/1991 | Young et al. . |

(List continued on next page.)

FOREIGN PATENT DOCUMENTS

0693276 A1  1/1996  European Pat. Off. .

OTHER PUBLICATIONS

Innovation Sports "The Significance of Protection" (undated).
Townsend ROM "Standard ROM Hinge" (undated).
Zinco Industries, Inc., "For the patient in kneed." (1989)
Sports Medicine Products (undated).
Bledsoe Brace Systems "The Bledsoe Ordering/Information Catalog" (undated).
Becker Orthopedic Appliance Company "Becker Orthopedic Presents The Polyaction™ Knee Orthosis" (undated).
Johnson & Johnson Orthopaedics "Masterhinge Adjustabrace and Adjustabrace II" (undated).
Innovation Sports "All a Knee Needs . . . from injury through rehab" (1987).

(List continued on next page.)

Primary Examiner—Linda C.M. Dvorak
Attorney, Agent, or Firm—James L. Ewing, IV; Geoff L. Sutcliffe; Kilpatrick Stockton LLP

[57] ABSTRACT

Hinges for orthopedic and rehabilitation braces allow intuitive, convenient and positive control and adjustment of the limits to which the braces may extend or flex. Such hinges also allow convenient locking of such braces. A flexion switch and an extension switch allow convenient repositioning of stops or limits which limit flexion and extension of the brace. Such switches may be repositioned, however, only with repositioning pressure for moving the switch to a new position combined with safety pressure for unlocking the switch. A brace locking switch may also be included. Such hinges promote more effective post-operative and rehabilitation results because they among other things allow users easily to change the flexion, extension and fixation limitations of their braces conveniently and in real time such as during post-operative and physical therapy sessions and workouts.

48 Claims, 5 Drawing Sheets

U.S. PATENT DOCUMENTS

| | | |
|---|---|---|
| 5,039,247 | 8/1991 | Young et al. . |
| 5,060,640 | 10/1991 | Rasmusson . |
| 5,078,127 | 1/1992 | Daneman et al. . |
| 5,105,805 | 4/1992 | Lapointe et al. . |
| 5,107,824 | 4/1992 | Rogers et al. . |
| 5,135,469 | 8/1992 | Castillo . |
| 5,244,455 | 9/1993 | Swicegood et al. . |
| 5,259,832 | 11/1993 | Townsend et al. . |
| 5,267,950 | 12/1993 | Weddendorf . |
| 5,292,303 | 3/1994 | Bastyr et al. . |
| 5,395,304 | 3/1995 | Tarr et al. . |
| 5,421,810 | 6/1995 | Davis et al. . |
| 5,460,599 | 10/1995 | Davis et al. . |
| 5,672,152 | 9/1997 | Mason et al. . |

OTHER PUBLICATIONS

Spademan "Embrace Comfort, The Spademan Progressive Post–op Brace" (undated).

Seton "Casting Procedure for Polyaction® Custom 45000" (undated).

Seton Products, Inc. "Seton Masterhinge Adjustabrace®" (Nov. 1986).

Wreck Wear "Lite Post–Op Rehab Brace 1030" (undated).

FLA Orthopedics, Inc. "FLA Orthopedics Knee Brace" (undated).

EZY Wrap "The ezy wrap® "1267"Hinged Knee Brace" (undated).

DynOrthotics LP "Knee Products" (undated).

Lenox Hill Brace Shop, Inc. "A Guide to ROM Control with the Lenox Hill® Derotation Brace" (undated).

DynOrthotics "CRM Rehabiliation Brace" (1991).

Lenox Hill "From A Name You Can Trust" (undated).

Smith & Nephew "For repairing cartilaginous defects, we're put the pieces together. Acufex MosaicPlasty" (1996).

Tosh Physical Therapy Sports Medicine West "Anterior Cruciate Ligament Rehabilitation" (Mar. 1996).

JOINT BRACE HINGES

The present invention relates to hinges for knee braces and for other braces such as those for the shoulder, elbow, hip or other body joints. Such hinges feature switches which may be intuitively, conveniently and positively positioned in order to limit joint flexion and extension or to fix the joint in a locked position for post-operative, rehabilitation or other desired purposes. The hinges preferably employ cammed surfaces and notches which cooperate with such switches for elegant and improved adjustable control of brace flexion, extension and fixation.

BACKGROUND OF THE INVENTION

Knee braces and braces for other joints are commonly employed after surgery or for treatment of injury to the joint. Such braces generally serve two major purposes. First, they brace or stabilize the joint in order generally to control its movement. Second, they limit joint flexion and/or extension in a controllable and adjustable fashion to prevent reinjury of the knee and to promote therapeutic and rehabilitation objectives.

Many braces have been devised to stabilize the knee and other joints and anatomical structures about various axes. Hinges which limit flexion and extension of the joint, such as those according to the present invention, may be employed, as a general matter, with or in any of such devices.

Bracing hinges for controllably limiting flexion and extension of the knee generally fall within one or more of several categories. A first category includes bicentric hinges in which a thigh bar and a calf bar of the brace couple to each other via a hinge which features two pivot points. Such braces have been said to replicate more accurately the motion of the knee joint, in which the condyles of the femur do not rotate relative to the tibial plateau about a fixed axis. (Instead, such braces seek to emulate changes in location of the instantaneous center of rotation of the tibia with respect to the femur as a function of the flexion angle.) Rotation (flexion and/or extension) of the thigh and calf bars relative to each other in these bicentric hinges is limited or controlled using members such as adjustably positionable rotatable cams (see, e.g., U.S. Pat. No. 4,554,913 to Womack, et al. which is incorporated herein by this reference), or interlocking teeth forming a portion of or connected to the thigh and calf bars which govern their position relative to each other. These devices have been constrained in flexion and extension in many ways, including use of gears and other structure (see, e.g., U.S. Pat. No. 4,697,583 to Mason, et al., U.S. Pat. No. 4,732,143 to Kansek, et al. and U.S. Pat. No. 5,060,640 to Rasmusson, all of which are incorporated herein by this reference).

A second general category of knee brace hinges employs a monocentric rather than a bicentric approach. The thigh and calf bars of the brace are coupled via a hinge which includes only one pivot point about which the thigh and calf bars pivot relative to one another. A number of conventional braces employ such monocentric hinges. These in turn often include structure for adjusting the limits to which the thigh and calf bars may rotate relative to one another, both in flexion and extension of the knee. For instance, U.S. Pat. No. 5,460,599 to Davis, et al., which is incorporated by this reference, employs rotatably positionable members with teeth and arcuate slots to receive and limit travel of pins which connect to the thigh and calf bars in order to limit their rotation relative to each other. U.S. Pat. No. 4,982,732 to Morris, which is incorporated by this reference, includes a generally circular housing that mounts a number of discrete sliding structures positioned at ten degree intervals on the housing. The sliding structures may be actuated or deactuated as desired to control flexion and extension of the brace and knee. U.S. Pat. No. 5,000,169 to Swicegood, which is incorporated by this reference, discloses a hinge which controls flexion and extension of the knee using a generally circular base whose periphery contains a number of indentations into which corresponding structure may be interposed to create limits on flexion and extension of the brace and knee. Other hinges employ generally circular plates coupled to the thigh and/or calf members. These plates feature a number of holes or indentations disposed at desired angular positions and into which pins, keys or similar structure may be placed in order to govern flexion and extension of the brace and knee. These conventional monocentric hinges generally incorporate designs that aim to limit patient access to or control over flexion, extension or fixation adjustments.

More recently, U.S. Pat. No. 5,672,152 shows a hinge for an orthopedic brace whose range of rotation may be adjusted by the user. The hinge features a rotation limiting stop provided at the peripheral edge of certain hinge members. The stop is selectively positionable in rotation limiting notches in the members to define an adjustable range of rotation. It can also lock the hinge against rotation in a locked mode of operation. A biasing assembly biases the stop in a radially inward direction to retain the stop in a selected position, but allows elastic radial displacement of the stop in a radially outward direction when a radially outward displacement force is externally applied to the stop. The notched peripheral hinge members of such hinges are exposed, however, and can catch or inadvertently be jammed by foreign objects or clothing which creates a potential for inadvertent operation of the hinge in a mode other than that corresponding to where the stops are placed. Additionally, the stops, which do not feature a positive locking action, can inadvertently catch and change position which again creates the potential of the hinge operating at limits other than those intended.

As post-operative procedures and rehabilitation procedures change and progress, the inventors have noted an increasing need for post-operative and rehabilitation braces which allow users to change and control flexion, extension or fixation of the relevant joint in intuitive and convenient fashion, yet which ensure that the braces maintain their proper limits. Various exercises prescribed in physical therapy, for instance, require the user to change the flexion and extension limits of the knee brace during a physical therapy session or workout. Braces whose hinges inhibit such adjustment typically degrade the effectiveness of such therapy, because patients sometimes simply do not bother to put themselves to the time or trouble necessary to manipulate pins, stops, thumb wheels or other sometimes cumbersome features which have conventionally been employed to adjust and control flexion and extension limits on braces of this sort. Yet such adjustability should not compromise the ability of the hinge to maintain proper limits and function effectively despite inadvertent shock or contact with clothing or foreign objects.

SUMMARY OF THE INVENTION

Braces according to the present invention feature hinges which allow intuitive, convenient and positive control of flexion, extension and fixation of the knee or other joint. Such hinges include a number of switches which may be conveniently positioned by the user in order to adjust and control knee flexion, extension and, if desired, fixation of the braces at various angular positions. Despite their convenience, the switches require no sacrifice in positive locking of the brace at the selected limits of flexion and extension; instead, they reduce or virtually eliminate the possibility that inadvertent repositioning and adjustment of flexion and extension limits could occur. In a preferred embodiment, such switches require downward pressure, combined with simultaneous sliding pressure relative to the brace, in order for unlocking and repositioning to occur. As a result, contact of the brace with nearby objects such as therapy equipment, for instance, does not generally cause repositioning of the switches and concomitant inadvertent change of flexion or extension limits. Similar switching mechanisms may be employed to lock the thigh and calf bars of braces in position relative to one another for various purposes as described more fully herein below.

It is accordingly an object of the present invention to provide orthopedic and rehabilitation braces with hinges which allow intuitive, convenient and positive control and adjustment of flexion, extension and fixation limits of the braces and the joints on which they are used.

It is an additional object of the present invention to provide orthopedic and rehabilitation braces whose flexion, extension and fixation limits may be adjusted easily and conveniently during therapy using one hand.

It is an additional object of the present invention to provide orthopedic and rehabilitation braces which allow convenient repositioning of flexion, extension and fixation limits via structure which requires deliberate manual pressure in order for repositioning and adjustment of flexion, extension and/or fixation limits to occur.

It is an additional object of the present invention to provide orthopedic and rehabilitation braces which allow convenient repositioning of flexion, extension and/or fixation limits via structure which requires pressure in two different directions simultaneously in order for repositioning and adjustment of flexion, extension and/or fixation limits to occur.

It is an additional object of the present invention to provide orthopedic and rehabilitation braces whose flexion, extension and/or fixation limits may be adjusted using tactile friendly structure for intuitive, convenient and positive control and locking of flexion, extension and/or fixation limits in order to promote better therapy and post-operative results.

It is an additional object of the present invention to provide orthopedic and rehabilitation braces which promote better post-operative and rehabilitation results using flexion, extension and/or fixation stops which may be easily repositioned, but which cannot generally be inadvertently repositioned.

It is an additional object of the present invention to provide orthopedic and rehabilitation braces whose flexion and/or extension limits may be adjusted using controllably positioned stops which bear against cammed surfaces and whose fixation limits may be adjusted using controllably positioned stops which bear against and lock relative to notched features.

Other objects, features and advantages of the present invention will become apparent with respect to the remainder of this document.

DETAILED DESCRIPTION OF THE DRAWINGS

Figures 1A, 1B:
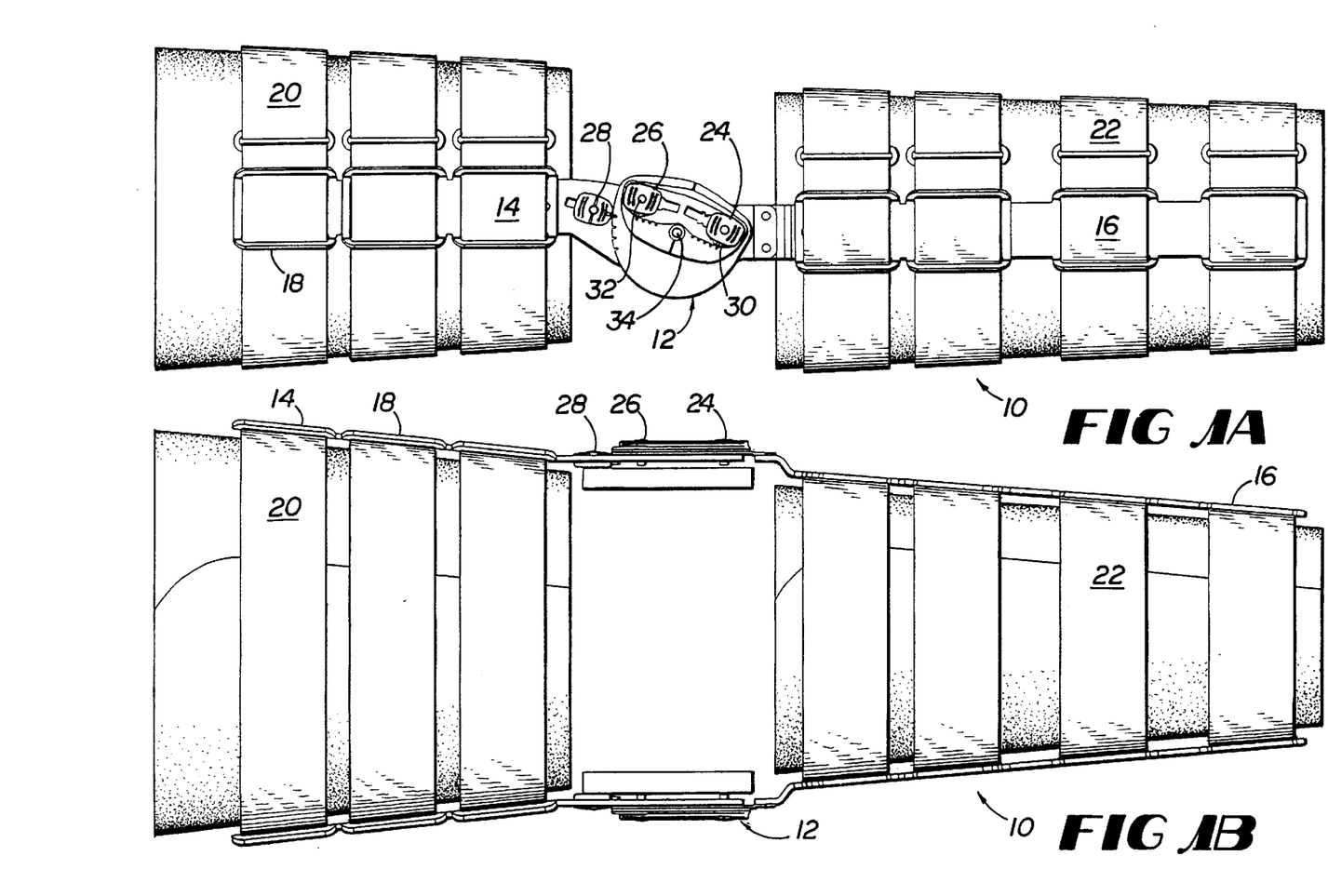
FIGS. 1A and 1B are schematic views of a brace which employs a monocentric hinge according to a preferred embodiment of the present invention.

FIG. 1 shows a brace 10 which employs a hinge 12 according to a preferred embodiment of the present invention. Brace 10 may be any post-operative or rehabilitation knee brace which is desired to govern flexion, extension and/or fixation of a desired joint in an adjustable and controllable manner. In the Figures included in this document, the brace 10 and hinge 12 and their components are shown in connection with a knee, in order to provide a proper and appropriate disclosure of one embodiment of the invention, but not in order to limit the scope or spirit of the invention in any way.

Hinge 12 as shown in the Figures, as a general matter, may be bicentric or monocentric or feature any other sort of connection as desired in order to couple a first bar and a second bar which correspond to body parts in the vicinity of the joint being braced. In the Figures, hinge 12 couples a thigh bar 14 and a calf bar 16. The assembly that includes thigh bar 14, hinge 12, and calf bar 16 appears on either side of the brace 10 shown in FIG. 1, although a hinge according to the present invention could be used on only one side of a brace as desired for particular applications. Thigh bars 14 and calf bars 16 can include structure such as slots or clips 18 for receiving or accommodating thigh straps 20, calf straps 22 or other structure for connecting thigh bars 14 and calf bars 16 to the user's thigh and calf. Such structure 18, 20 and 22 is generally conventional in nature and may be fashioned of conventional materials and oriented and manufactured as desired in order to achieve the desired results in a particular knee brace.

FIG. 1 shows a hinge 12 according to the present invention with a flexion switch 24, extension switch 26 and lock or fixation switch 28 for adjustably controlling rotation of thigh bar 14 and calf bar 16 relative to each other, and thus flexion and extension of the brace 10 and the knee to which the brace is applied and for creating fixation of the brace and leg if desired. Hinges 12 according to the present invention may exclude lock switch 28, flexion switch 24 or extension switch 26, or any combination of them, as desired, although it is more likely that if any of these are omitted, it would be lock switch 28.

As shown in FIG. 1, each switch 24, 26, 28 can feature an interface 30 and lock button 32, or other structure, for adjusting flexion, extension and locking of the brace 10 and hinge 12. Lock button 32 is pressed in a downward fashion relative to the hinge in order to create a mode in which interface 30 may then be manipulated in a sliding fashion substantially perpendicular to the direction of pressure on button 32, in order for repositioning of switches 24, 26 and/or 28. Thus appropriate for the present invention is a switch structure which requires force or pressure in at least two different directions simultaneously for unlocking and repositioning of the switch to occur. Also appropriate is switch structure which allows convenient repositioning of switches 24, 26, 28 only with deliberate force or pressure but not generally with inadvertently applied force or pressure.

Hinge 12 shown in FIG. 1 is a monocentric hinge structure using a single pin 34 which may be a rivet, bolt or any other desired fastener. Likewise, hinge 12 can, if desired, be a bicentric hinge or allow coupling of thigh bar 14 and calf bar 16 according to any other structure, theory or design which permits use of the cammed surfaces, notches, other surface features, and switches according to the present invention.

Figure 2:
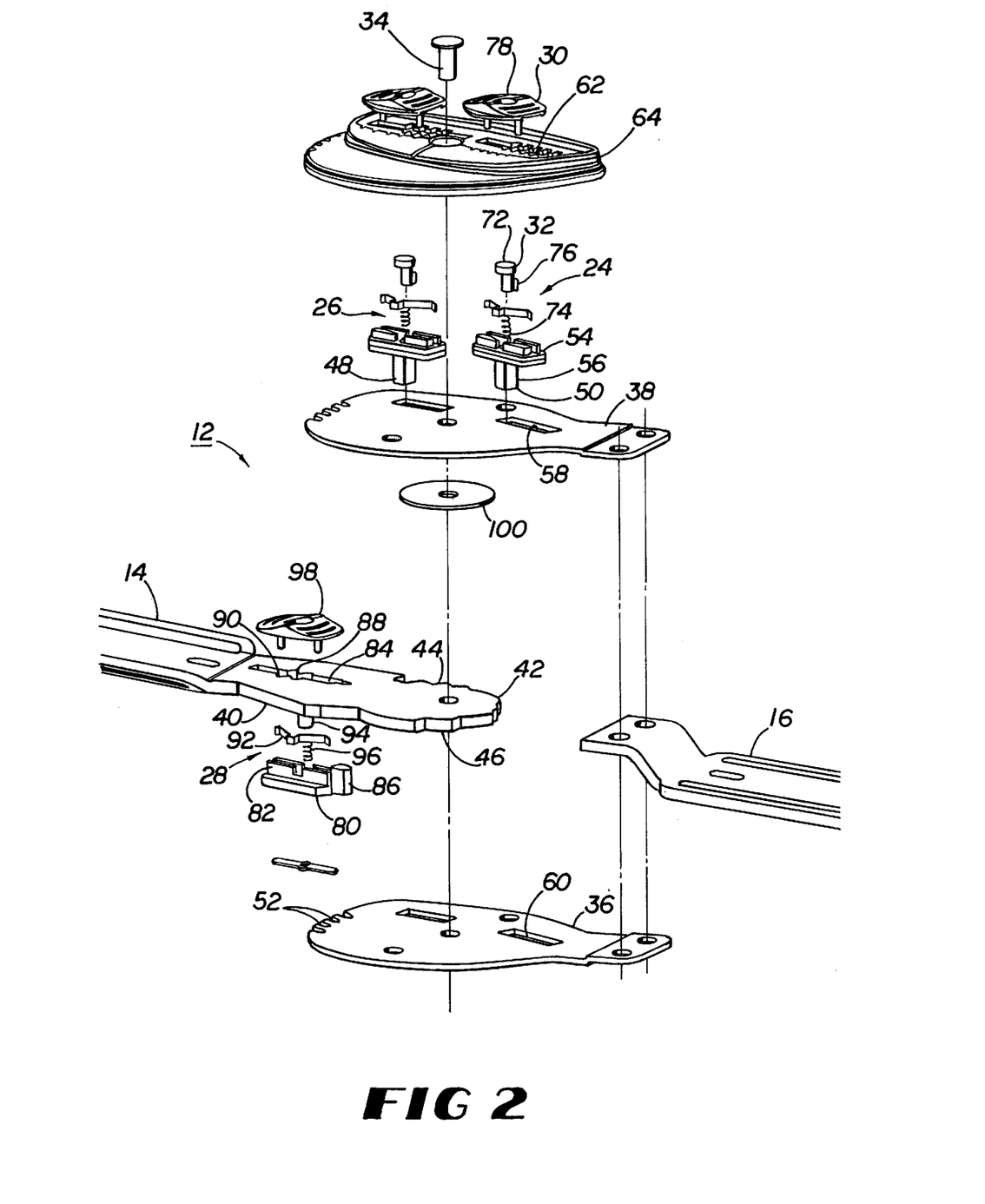
FIG. 2 is an exploded perspective view of a portion of the hinge of FIG. 1.

FIG. 2 is an exploded perspective view showing relationship of components of hinge 12. In the preferred embodiment as shown in FIG. 2, hinge 12 includes a plurality of plates which are connected to thigh bar 14 and calf bar 16 and which rotate relative to one another about pin 34. The particular embodiment shown in FIG. 2 contains a calf bar bottom plate 36 and a calf bar top plate 38 which are connected via rivets to calf bar 16. Thigh bar plate 40 is formed as a portion of thigh bar 14 and is adapted to rotate about pin 34 relative to calf bar top plate and bottom plate 36, 38. Calf bar top and bottom plates 36, 38 may be formed as part of calf bar 16 or attached as desired to calf bar 16 (such formation or attachment of plates to bars considered in this document to be included in the meaning of the term "connected"). A pair of calf bar plates 36, 38 is not required; one plate could suffice, as could more; the number and disposition of plates is not critical to the invention. Calf bar 16 may be connected to a single plate such as with a cammed surface of the sort characterized by thigh bar plate 40, and thigh bar 14 connected to top and bottom plates similar to the calf bar top and bottom plates 36 and 38. Various switches 24, 26, 28 may be positioned relative to plates 36, 38, 40 as desired, and not necessarily according to the structure shown in FIG. 2, in order to create the intuitive, convenient and positive control of flexion and extension, and locking, of braces and knees according to the present invention.

As shown in the particular embodiment of FIG. 2, thigh bar plate 40 contains a cammed surface 42 which in turn features a number of extension limiting lands 44 and flexion limiting lands 46. Extension limiting lands 44 cooperate with extension stop 48 which may be adjusted in a position to bear against any desired extension land 44 in order to control and limit flexion of thigh bar 14 relative to calf bar 16. Similarly, flexion limiting lands 46 of thigh bar plate 40 bear against flexion stop 50 which may be adjustably positioned to bear against a desired land in order to limit flexion of thigh bar 14 relative to calf bar 16. Again, it may be the calf bar 16 that is instead coupled to cammed surface 42 so that stops 48 and 50 would be connected to the thigh bar 48 rather than the calf bar 16.

FIG. 2 also shows lock switch 28 connected to thigh bar plate 40 which may be positioned to cooperate with indentations 52 on calf bar top plate and bottom plate 36, 38 respectively in order to lock thigh bar 14 and calf bar 16 in position relative to each other at different angles of flexion/extension. Indentations 52 may just as easily be placed as desired on a plate bearing a cammed surface or thigh bar plate 40 in order to cooperate with a lock switch 28 placed anywhere as desired to allow adjustable locking of thigh bar 14 and calf bar 16 relative to each other.

Figure 3:
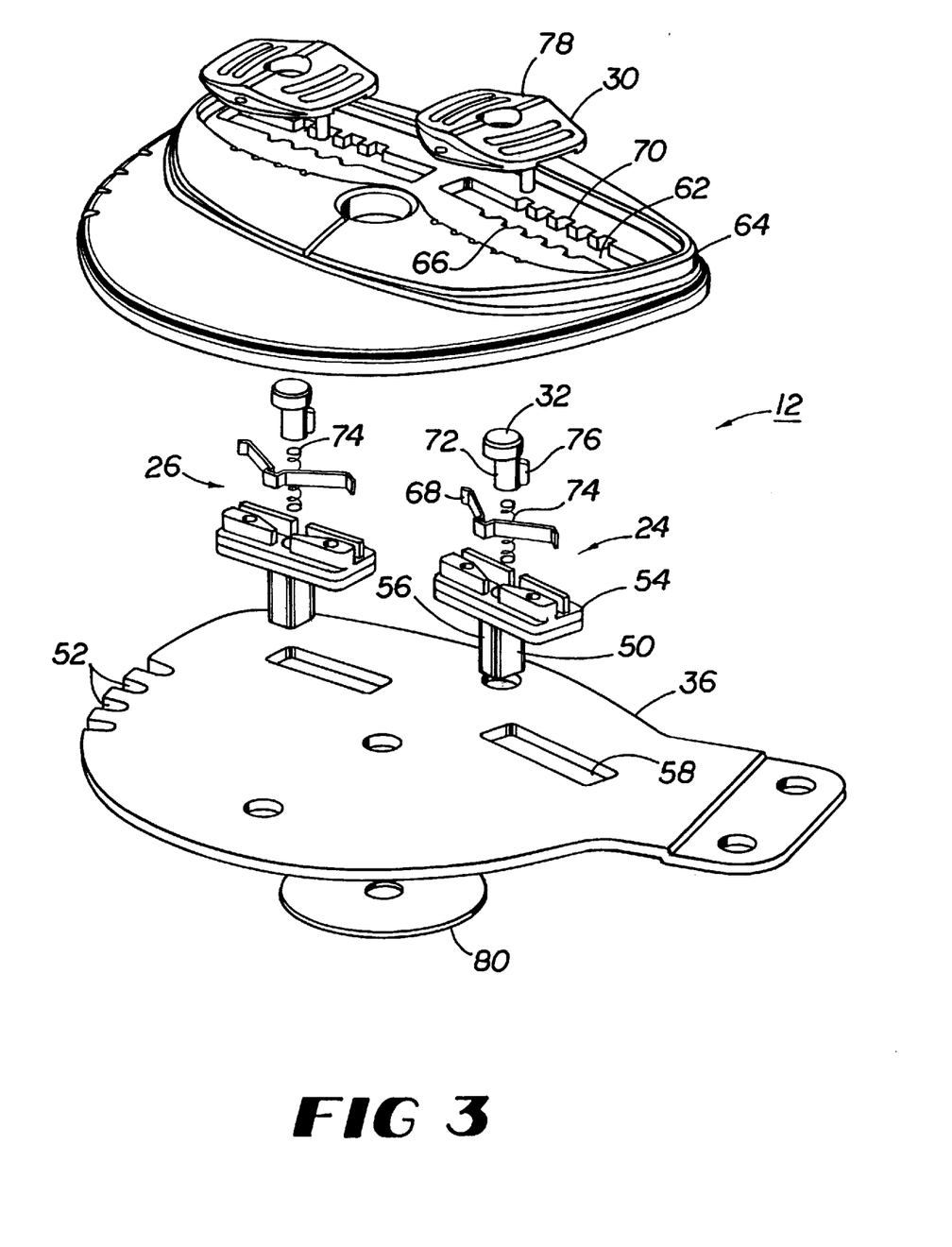
FIG. 3 is a second exploded perspective view of a portion of the hinge of FIG. 1.
Figure 4:
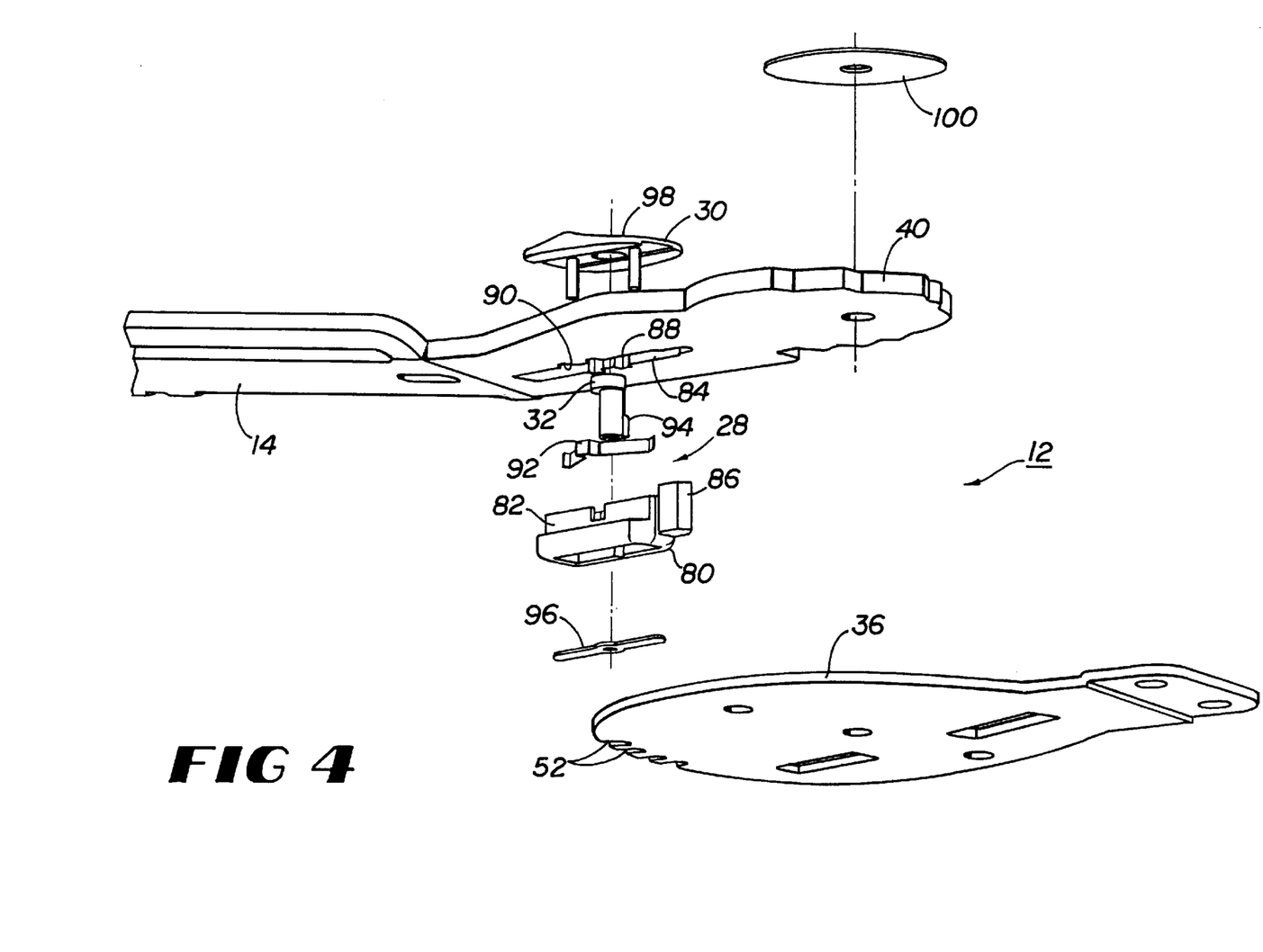
FIG. 4 is a third exploded perspective view of a portion of the hinge of FIG. 1.

FIGS. 2, 3 and 4 show a preferred embodiment for structuring flexion switch 24, extension switch 26 and/or locking switch 28. Switches 24 and 26 as shown in these figures feature the same sort of structure, which is slightly different from the structure of the switch 28, but that need not be so. The structures of all of these switches may be the same or different to accommodate various requirements. Additionally, as mentioned above, various other structural components are easily equivalent with, interchangeable with, or constitute insubstantial changes to any or all of the components of switches 24, 26 or 28 and their cooperating structure to allow intuitive, convenient and positive adjustable control of flexion and extension limitation of thigh bar 14 and calf bar 16 relative to each other, and thus limitation on flexion, extension and/or fixation of brace 10 and the knee on which it is positioned. A requirement is that such mechanisms allow the user conveniently to reposition limits or stops, preferably with one hand, to control extension, flexion and/or fixation of bars 14 and 16, with virtual or complete prevention of inadvertent repositioning of such stops or limits. More particularly, a narrower requirement is that the structure permit convenient repositioning of flexion, extension and/or fixation components only upon application of simultaneous pressure in at least two different directions in order to free or unlock such components to move and to reposition them.

As shown in the particular structure illustrated in FIGS. 2–3, flexion switch 24, which is structured similarly to extension switch 26, features a trolley 54 which includes a stop 56 that protrudes through stop slots 58 and 60 in calf bar top plate 38 and bottom plate 36, respectively. Trolley 54 with stop 56 may be dimensioned and formed as desired in order to cause the stop 56 to be in a position to bear against flexion lands 46 on thigh bar plate 40. Additionally, positioning and dimensioning of slots 58, 60 and lands 46 of cammed surface 42 to allow stop 56 to bear against an appropriate land 46 on cammed surface 42 to create a desired limit of flexion is carried out using empirical or observed analysis. Preferably the lands 46 are oriented so that when positioned against stop 56, they do not impose any lateral or other unintended force to stop 56 that would impose an undesired load on the detent notches 66. None of this is required for the invention to work. What is required in conjunction with positioning of stop 56 and configuration of lands 46 and cammed surface 42 generally is that the geometry and structure allow stop 56 to bear properly against the appropriate lands 46 in order for the brace 10 to wear well and absorb considerable load cycles over time during course of its life.

Trolley 54 is constrained in a sliding relationship relative to stop slots 58 and 60, in the preferred embodiment, via a notched track 62 in face plate 64 of hinge 12. Thus, when face plate 64 is in position on calf bar top plate 38, trolley 54 translates back and forth in track 62 so that stop 56 may be adjustably positioned to protrude through stop slots 58 and 60 in order to bear against different lands 46 on cammed surface 42 of thigh bar plate 40.

Trolley 54 and its stop 56 are further constrained in movement by a plurality of detent notches 66 formed in a first side of notched track 62 on face plate 64. A detent 68, which may be a leaf spring, a member biased by a coil spring or other desired structure, or part of trolley 54, is adapted to protrude into a detent notch 66 in order to index the sliding movement of trolley 54 and stop 56 in track 62 and thus limit the number of positions in track 62 in which trolley 54 may be placed (which correspond to place stop 56 in registration with corresponding lands 46).

In addition to detent notches 66, notched track 62 in face plate 64 also features a plurality of locking notches 70 which may be the same as or different from detent notches 66. In the illustrated embodiment shown in FIGS. 2–4, locking notches 70 are located on the side of notched track 62 opposite from detent notches 66. A safety lock 72 protrudes through the outer surface of face plate 64 and is biased away from trolley 54 and upward through face plate 64 using a spring or other biasing mechanism 74. The safety lock 72 features a key 76 which, when spring 74 biases safety lock 72 away from trolley, engages a locking notch 70 in notch track 62 to lock trolley 54 in place and thus stop 56 in place relative to a particular flexion limiting land 46. When suitable pressure from a finger or thumb pushes safety lock 72 into or toward face plate 64, key 76 moves downward and disengages from locking notch 70 which then allows trolley 54 to slide in notched track 62 and stop 56 to be repositioned in order to change flexion limits.

The user interface 30 for flexion switch 24 includes not only a safety lock 72, but also an interface plate 78 which may be fashioned as desired for comfortable and proper fit, form and function in order to allow the user to slide the trolley 54 in notched track 62. Safety lock 72 in the preferred embodiment protrudes through interface plate 78 to allow the user to be able simultaneously to push lock 72 in order to disengage key 76 from locking notch 70 and to slide trolley 54 in notched track 62 until the detent 68 is received in the appropriate detent notch 66 to correspond to a desired degree of flexion of brace 10. Hinge face plate 64 may feature indicia to show angles of flexion and/or extension limitation that correspond to locking notches 70, detent notches 66 and the workings of lands 44, 46 and stops of the switches 24, 26 of the present invention.

Key 76 may be positioned to bias detent 68 further into a detent notch 66 in order to create a locking relationship, in which event locking notches 70 and detent notches 66 may be the same. Other structural versions are obviously easily imaginable to allow a switch 24 which accommodates the scope and spirit of this invention. As merely one example, switches according to the present invention may contain cammed surfaces themselves, with or without lands, and be structured to rotate relative to the face plate 64 in proper indexing and conveniently releasable locking relationship in order to place desired portions of their cammed surfaces against portions of the cammed surface 42 for intuitive, convenient and positive control of flexion and/or extension of the brace 10.

In the preferred embodiment, extension switch 26 is structured identically or virtually identically to flexion switch 24 and operates in the same general fashion, but is positionable in other directions to control extension of brace 10 and the knee on which it is positioned.

Lock switch 28 in the preferred embodiment shown in FIGS. 2 and 4 contains a trolley 80 with a tracking portion 82 which is adapted to slide in notched track 84 of thigh bar plate 40. A protrusion 86 on trolley 80 is adapted to protrude into one of the indentations 52 on calf bar top plate and bottom plate 36, 38 when switch 28 is positioned to the "engaged" position. Thus, notched track 84 features a pair of locking notches 88 (and, in the embodiment shown in FIGS. 2 and 4, detent notches 90). A detent 92 positioned relative to trolley 80 contains a portion which is received by one of the detent notches 90 to hold switch 28 in place in a releasable fashion. A safety lock 94 biased with a biasing mechanism 96 similar to or the same as biasing mechanism 74, operates, as does safety lock 72, to retain switch 28 in position relative to thigh bar plate 40 when safety lock 94 is not being actuated or depressed. Interface 98, which may be similar to interface 78 in appearance and structure, if desired, allows the user to slide trolley 80 into and out of engaging relationship with calf bar top and bottom plates 36, 38 in order to lock hinge 12 and brace 10 in various angular positions as desired. Lock switch 28 may, as one simple example of alternative structure, appear on face plate 62 and cooperate with indentations in thigh bar 40.

Various washers 100 or other friction diminishing or lubricating devices as desired or required may be used. In the preferred embodiment, the hinge 12 may contain washers 100 such as conventional delrin washers between calf bar plates 36, 38 and thigh bar plate 40 and at other places if desired.

Figure 5A:
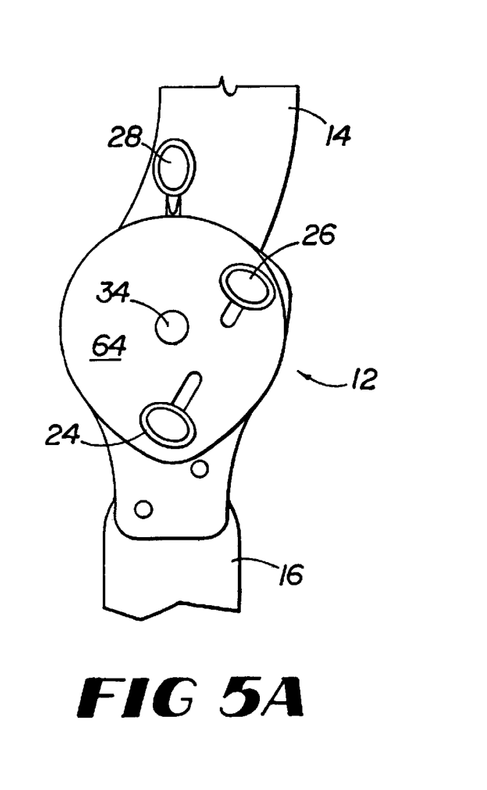
FIGS. 5A, 5B and 5C are schematic views of the hinge of FIG. 1 shown in various positions.

FIG. 5 is a schematic drawing which shows at (A) the flexion switch and extension switches 24, 26 in position to allow full extension [substantially 0 degrees between thigh bar 14 and calf bar 16 (zero degrees taking into account manufacturing and wear tolerances)] of hinge 12 and full flexion (substantially 140 degrees between thigh bar 14 and calf bar 16). The locking switch 28 is unengaged.

Figure 5B:
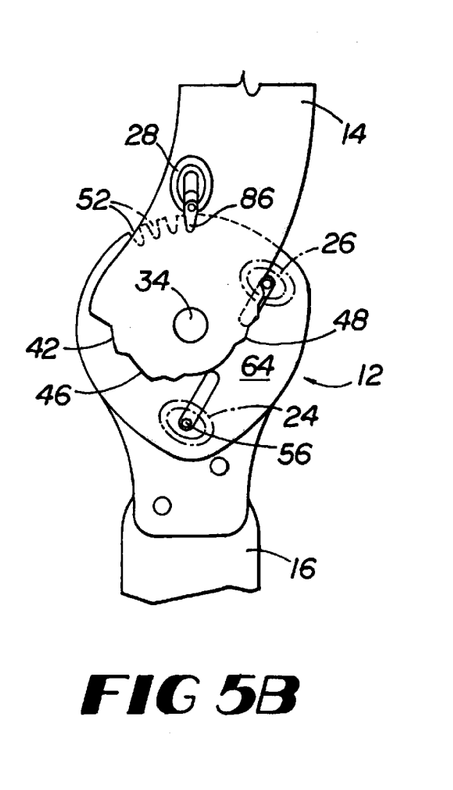

FIG. 5 at (B) shows the flexion switch 24 and extension switch 26 in the same positions but with the locking switch 28 engaged to lock thigh bar 14 and calf bar 16 in position relative to each other at full extension.

Figure 5C:
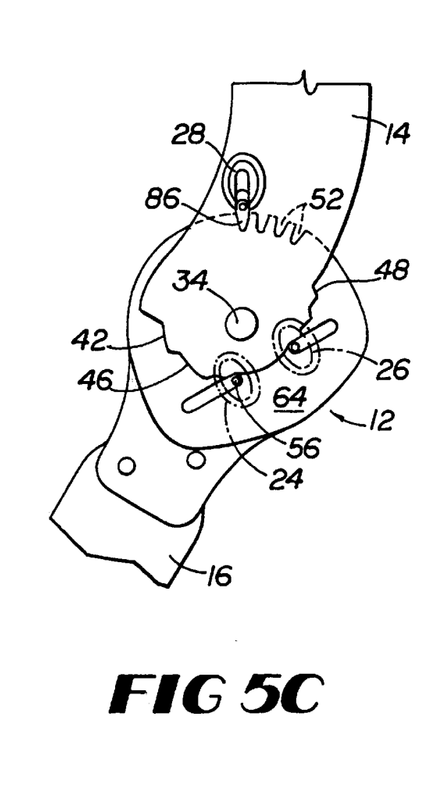

FIG. 5 at (C) shows the locking switch 28 engaged to lock thigh bar 14 and calf bar 16 in angular relationship to each other. Locking switch 28 preferably operates independently of flexion switch 24 and extension switch 26 to lock the brace into a desired position. For example, locking switch 28 may be set as desired without the need to set flexion switch 24 and/or extension switch 26 in any particular position (so long as there is no interference) to lock the brace in desired position. If locking switch 28 as shown at (C) in FIG. 5 were disengaged, flexion switch 24 is positioned for substantially 30 degrees flexion of thigh bar 14 and calf bar 16 relative to each other, and extension switch 26 is positioned for substantially 30 degrees.

In the preferred embodiment as shown in FIGS. 1–5, extension switch 26 and its corresponding components together with corresponding portions of the calf bar bottom plate and top plate 36, 38 and thigh bar plate 40 are structured to allow maximum extension at 0, 10, 20, and 30 degrees between thigh bar 14 and calf bar 16, respectively. Again, in the preferred embodiment, flexion switch 24 and these corresponding components are adapted to permit maximum flexion of brace 10 to occur at 30, 40, 70, 90 and 140 degrees between thigh bar 14 and calf bar 16, respectively. Various configurations of various portions of calf bar bottom plate and top plate 36, 38, thigh bar 40, cammed surface 42, lands 44 and 46 and switches 24, 26 to create a hinge 12 that contains any desired set of maximum extension and flexion limitations (of any joint) is readily accomplished according to the teachings of this invention and is within the purview of those accustomed to designing and making knee braces.

The foregoing is provided for purposes of illustration and disclosure of a preferred embodiment of hinges according to the present invention. Modification, adaptations, omissions and additions to the structure disclosed herein, including (without limitation) provision of equivalent, interchangeable or alternative structure which accomplishes substantially the same results as the disclosed structure, or constitutes an insubstantial change to it, fall within the scope and spirit of the invention.

What is claimed is:

1. A hinge for a body joint brace which hinge is adapted to couple a first bar and a second bar of the brace, the hinge comprising:
   a. a first member adapted to be connected to one of the first bar and the second bar, and having a plurality of lands;
   b. a second member adapted to be connected to the other of the first bar and the second bar, and being rotatable with respect to the first member; and
   c. a switch moveable with the second member and comprising a stop that is selectively placed at any one of a plurality of positions relative to the second member, each of the plurality of positions being associated with a corresponding land on the first member;

wherein the stop bears against one of the plurality of lands on the first member in order to limit rotation of the first member relative to the second member and the lands are spaced from each other so that the stop contacts the lands at different angles of rotation of the first member relative to the second member.

2. A hinge according to claim 1 in which the first member is connected to the first bar and the second member is connected to the second bar.

3. A hinge according to claim 1 in which the first member is connected to the second bar and the second member is connected to the first bar.

4. A hinge according to claim 1 in which the first member is formed as part of the first bar and the second member comprises a pair of first bar plates which are attached to the second bar.

5. A hinge according to claim 1 in which the lands are flexion limiting lands, the switch is a flexion switch, and the stop is adapted to bear against selected flexion limiting lands for adjustably limiting flexion of the brace.

6. A hinge according to claim 5 in which the first member further includes a plurality of extension limiting lands and the second member further includes an extension switch having a stop adapted to bear against selected extension limiting lands for adjustably limiting extension of the brace.

7. A hinge according to claim 1 in which the switch includes structure adapted to interpose force between the second member and the switch for engaging the switch in position relative to the second member.

8. A hinge according to claim 1 in which the switch contains structure adapted to retain the switch in place relative to the second member in one of the plurality of positions and in convenient releasable fashion, thereby indexing the switch relative to the second member.

9. A hinge according to claim 1 in which the switch contains structure adapted to interpose force between the second member and the switch for engaging the switch in position relative to the second member, and structure adapted to retain the switch in place relative to the second member in one of the plurality of positions and in conveniently releasable fashion, thereby indexing the switch relative to the second member.

10. A hinge according to claim 9 in which the structure for engaging the switch in position relative to the second member and the structure adapted to retain the switch in place relative to the second member comprise at least some of the same components.

11. A hinge according to claim 1 in which the switch is adapted to be repositioned relative to the second member only with deliberate force.

12. A hinge for a body joint brace which hinge is adapted to couple a first bar and a second bar of the brace, the hinge comprising:

a. a first member connected to one of the first bar and the second bar, and containing at least one cammed surface; and b. a second member connected to the other of the first bar and the second bar, the second member connected in sliding fashion to a switch, the switch comprising a stop and adapted to slide and be repositioned relative to the second member so that the stop is positioned to bear against at least one portion of the cammed surface of the first member in order to limit rotation of the first bar and the second bar relative to each other and thus movement of the body joint;

the switch contains structure adapted to interpose force between the second member and the switch for engaging the switch in position relative to the second member, and structure adapted to retain the switch in place relative to the second member in a plurality of preselected positions and in conveniently releasable fashion, thereby indexing the switch relative to the second member;

wherein the structure for engaging the switch in position relative to the second member comprises a plurality of indentations in the second member and a key connected to the switch which is adapted to engage selected ones of the indentations.

13. A hinge for a body joint brace which hinge is adapted to couple a first bar and a second bar of the brace, the hinge comprising:

a. a first member connected to one of the first bar and the second bar, and containing at least one cammed surface; and b. a second member connected to the other of the first bar and the second bar, the second member connected in sliding fashion to a switch, the switch comprising a stop and adapted to slide and be repositioned relative to the second member so that the stop is positioned to bear against at least one portion of the cammed surface of the first member in order to limit rotation of the first bar and the second bar relative to each other and thus movement of the body joint;

the switch contains structure adapted to interpose force between the second member and the switch for engaging the switch in position relative to the second member, and structure adapted to retain the switch in place relative to the second member in a plurality of preselected positions and in conveniently releasable fashion, thereby indexing the switch relative to the second member;

wherein the structure adapted to retain the switch in place relative to the second member comprises a plurality of indentations in the second member and a detent connected to the switch, a portion of which detent is adapted to cooperate with selected ones of the indentations in order to index the switch on the second member.

14. A hinge for a body joint brace which hinge is adapted to couple a first bar and a second bar of the brace, the hinge comprising:

a. a first member connected to one of the first bar and the second bar, and containing at least one cammed surface; and b. a second member connected to the other of the first bar and the second bar, the second member connected in sliding fashion to a switch, the switch comprising a stop and adapted to slide and be repositioned relative to the second member so that the stop is positioned to bear against at least one portion of the cammed surface of the first member in order to limit rotation of the first bar and the second bar relative to each other and thus movement of the body joint;

wherein the switch is adapted to be repositioned relative to the second member only with force applied to the switch in two different directions simultaneously.

15. A hinge according to claim 14 in which the switch is adapted to be repositioned relative to the second member only with force applied to slide the switch relative to the second member simultaneously with application of another force to the switch in order to unlock the switch relative to the second member.

16. A hinge for a knee brace, said hinge adapted to couple a thigh bar to a calf bar of the brace, said hinge comprising:
   a. a first member adapted to be connected to one of the thigh bar and the calf bar and containing a first surface internal of the hinge;
   b. a second member adapted to be connected to the other of the thigh bar and the calf bar; and
   c. a switch connected in adjustably positionable fashion to the second member, said switch containing structure which is adapted to cooperate with the first surface of the first member as the switch is adjusted in position in order to limit movement of the first and second members relative to each other without being exposed to foreign objects in the vicinity of the hinge, the switch including a disengagement structure which cooperates with portions of the second member and which is adapted to lock the switch in position on the second member without locking the switch in position on the first member, the position of said switch adapted to be adjusted only when pressure is applied to a portion of the switch which causes at least partial disengagement of the switch with the second member thus permitting relative motion between the switch and the second member, at the same time a different force is applied to position the switch.

17. A hinge according to claim 16 in which the first surface is a cammed surface.

18. A hinge according to claim 17 in which the switch is connected to the second member in sliding fashion.

19. A hinge according to claim 16 in which the first surface is a cammed surface and the switch contains a cammed surface for bearing against the cammed surface of the first member.

20. A hinge according to claim 18 comprising two switches, a first for limiting flexion of the thigh bar and the calf bar of the brace relative to each other and thus flexion of the knee, and the second for limiting extension of the thigh bar and the calf bar of the brace relative to each other and thus extension of the knee.

21. A hinge according to claim 18 in which the switch additionally comprises structure adapted to retain the switch in place relative to the second member in a plurality of preselected positions and in conveniently releasable fashion, thereby indexing the switch relative to the second member.

22. A hinge according to claim 16 in which the first member is connected to the thigh bar and the second member is connected to the calf bar.

23. A hinge according to claim 16 in which the first member is formed as part of the thigh bar and the second member comprises a pair of calf bar plates which are attached to the calf bar.

24. A hinge according to claim 16 further comprising a locking switch connected to one of the first and second members, and adapted to engage selected ones of a plurality of indentations in the other of the first and second members, for locking the thigh bar of the brace in position relative to the calf bar in predetermined positions.

25. A hinge for a knee brace, the hinge adapted to couple a thigh bar to a calf bar of the brace, said hinge comprising:
   a. a first member adapted to be connected to one of the thigh and calf bar and containing a cammed surface which features a plurality of lands;
   b. a second member adapted to be connected to the other of the thigh and calf bar and hinged to said first member; and
   c. a switch connected in slidably positionable fashion to the second member, which switch comprises:
      (i) a stop adapted to bear against selected ones of the lands corresponding to the position of the switch relative to the second member;
      (ii) structure adapted to interpose force between the second member and the switch for engaging the switch in position relative to the second member;
      (iii) structure adapted to retain the switch in place relative to the second member in a plurality of preselected positions and in conveniently releasable fashion, thereby indexing the switch relative to the second member;
      (iv) whereby the switch is adapted to be repositioned relative to the second member only with application of deliberate force.

26. A hinge according to claim 25 comprising lands adapted to limit extension of the brace and an extension switch connected in slidably positionable fashion to the second member.

27. A hinge according to claim 25 comprising lands adapted to limit flexion of the brace and a flexion switch connected in slidably positionable fashion to the second member.

28. A hinge according to claim 25 in which the first member is connected to the thigh bar and the second member is connected to the calf bar.

29. A hinge according to claim 25 in which the first member is formed as part of the thigh bar and the second member comprises a pair of calf bar plates which are fastened to the calf bar.

30. A hinge according to claim 25 further comprising a locking switch connected to one of the first and second members, and adapted to engage selected ones of a plurality of indentations in the other of the first and second members, for locking the thigh bar of the brace in position relative to the calf bar in predetermined positions.

31. A hinge according to claim 25 in which at least some of the lands are adapted in shape to impose no lateral force on the retaining structure when the lands are positioned against the stop.

32. A hinge for a knee brace, the hinge adapted to couple a thigh bar to a calf bar of the brace, said hinge comprising:
   a. a first member adapted to be connected to one of the thigh and calf bar and containing a cammed surface which features a plurality of lands;
   b. a second member adapted to be connected to the other of the thigh and calf bar and hinged to said first member; and
   c. a switch connected in slidably positionable fashion to the second member, which switch comprises:
      (i) a stop adapted to bear against selected ones of the lands corresponding to the position of the switch relative to the second member;
      (ii) structure adapted to interpose force between the second member and the switch for engaging the switch in position relative to the second member;
      (iii) structure adapted to retain the switch in place relative to the second member in a plurality of preselected positions and in conveniently releasable fashion, thereby indexing the switch relative to the second member;
      (iv) whereby the switch is adapted to be repositioned relative to the second member only with application of deliberate force;
   wherein the structure for engaging the switch in position relative to the second member comprises a plurality of indentations in the second member and a key connected to the switch which is adapted to engage selected ones of the indentations.

33. A hinge for a knee brace, the hinge adapted to couple a thigh bar to a calf bar of the brace, said hinge comprising:
   a. a first member adapted to be connected to one of the thigh and calf bar and containing a cammed surface which features a plurality of lands;

b. a second member adapted to be connected to the other of the thigh and calf bar and hinged to said first member; and c. a switch connected in slidably positionable fashion to the second member, which switch comprises:
  (i) a stop adapted to bear against selected ones of the lands corresponding to the position of the switch relative to the second member;
  (ii) structure adapted to interpose force between the second member and the switch for engaging the switch in position relative to the second member;
  (iii) structure adapted to retain the switch in place relative to the second member in a plurality of preselected positions and in conveniently releasable fashion, thereby indexing the switch relative to the second member;
  (iv) whereby the switch is adapted to be repositioned relative to the second member only with application of deliberate force;

wherein the structure adapted to retain the switch in place relative to the second member comprises a plurality of indentations in the second member and a detent connected to the switch, a portion of which detent is adapted to cooperate with selected ones of the indentations.

34. A knee brace comprising:
a. a pair of thigh bars;
b. a pair of calf bars;
c. structure for connecting the thigh bars to the thigh of a user and for connecting the calf bars to the corresponding calf of the user; and
d. at least one hinge for coupling one of the thigh bars to one of the calf bars, and for controlling flexion and extension of the corresponding knee, the hinge comprising:
  (i) a first member connected to one of the thigh bar and the calf bar and containing a cammed surface featuring a plurality of lands;
  (ii) a second member connected to the other of the thigh bar and the calf bar;
  (iii) a flexion switch connected in adjustably positionable fashion to the second member, said flexion switch containing structure which is adapted to bear against different lands of the cammed surface of the first member as the switch is adjusted in position, the position of said switch adapted to be adjusted only when pressure is applied to a portion of the switch which causes at least partial disengagement of the switch with the second member thus permitting relative motion between the switch and the second member, at the same time a different force is applied to position the switch; and
  (iv) an extension switch connected in adjustably positionable fashion to the second member, said extension switch containing structure which is adapted to bear against different lands of the cammed surface of the first member as the switch is adjusted in position, the position of said switch adapted to be adjusted only when pressure is applied to a portion of the switch which causes at least partial disengagement of the switch with the second member thus permitting relative motion between the switch and the second member, at the same time a different force is applied to position the switch.

35. A brace according to claim 34 in which the switches are connected to the second member in sliding fashion.

36. A brace according to claim 34 in which at least one of the switches contains a cammed surface for bearing against the cammed surface of the first member.

37. A brace according to claim 34 in which the switches additionally comprise structure adapted to retain them in place relative to the second member in a plurality of preselected positions and in conveniently releasable fashion, thereby indexing the switches relative to the second member.

38. A brace according to claim 34 in which the first member is connected to the thigh bar and the second member is connected to the calf bar.

39. A brace according to claim 34 in which the first member is formed as part of the thigh bar and the second member comprises a pair of calf bar plates which are fastened to the calf bar.

40. A brace according to claim 34 further comprising a locking switch connected to one of the first and second members, and adapted to engage selected ones of a plurality of indentations in the other of the first and second members, for locking the thigh bar of the brace in position relative to the calf bar in predetermined positions.

41. A hinge for a body joint brace which hinge is adapted to couple a first bar and a second bar of the brace, the hinge comprising:
  a. a first member adapted to be connected to one of the first bar and the second bar, and containing at least one stop surface;
  b. a second member adapted to be connected to the other of the first bar and the second bar;
  c. a stop that is selectively secured in any one of a plurality of positions relative to the second member, the stop bearing against at least one portion of the stop surface of the first member in order to limit rotation of the first member relative to the second member; and
  d. an interface connected to the stop for selectively disengaging the stop from the second member and for permitting the stop to be placed in a desired one of the plurality of positions, the plurality of positions limiting rotation of the first member relative to the second member at different angles of rotation.

42. The hinge as set forth in claim 41, further including a face plate having a plurality of notches for defining the plurality of positions.

43. The hinge as set forth in claim 42, further including a key, connected to the stop, for being engaged within one of the notches.

44. The hinge as set forth in claim 41, wherein the second member includes a plurality of lands for defining the different angles of rotation.

45. The hinge as set forth in claim 41, wherein the interface includes a plate that is connected to the stop and that is maneuvered by a user to place the stop in the desired one of the plurality of positions.

46. The hinge as set forth in claim 41, wherein the interface includes a safety lock for selectively engaging the stop in the desired one of the plurality of positions.

47. The hinge as set forth in claim 41, further including a lock switch for locking the first member relative to the second member.

48. The hinge as set forth in claim 41, wherein the stop is an extension stop for limiting an extension of the joint, the first member includes a second stop surface, and the hinge further includes a flexion stop for contacting the second stop surface for limiting flexion of the joint.

\* \* \* \* \*